(12) United States Patent
Usuda

(10) Patent No.: US 12,213,641 B2
(45) Date of Patent: Feb. 4, 2025

(54) IMAGE PROCESSING APPARATUS AND IMAGE PROCESSING METHOD

(71) Applicant: FUJIFILM Corporation, Tokyo (JP)

(72) Inventor: Toshihiro Usuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 997 days.

(21) Appl. No.: 17/200,914

(22) Filed: Mar. 15, 2021

(65) Prior Publication Data
US 2021/0196101 A1 Jul. 1, 2021

Related U.S. Application Data

(63) Continuation of application No. PCT/JP2019/033598, filed on Aug. 28, 2019.

(30) Foreign Application Priority Data

Sep. 21, 2018 (JP) ................................. 2018-177437

(51) Int. Cl.
A61B 1/00 (2006.01)
A61B 1/06 (2006.01)
(Continued)

(52) U.S. Cl.
CPC .... *A61B 1/00006* (2013.01); *A61B 1/000094* (2022.02); *A61B 1/000095* (2022.02);
(Continued)

(58) Field of Classification Search
CPC .......... A61B 1/00006; A61B 1/000094; A61B 1/000095; A61B 1/0655; A61B 1/00045;
(Continued)

(56) References Cited

U.S. PATENT DOCUMENTS

2018/0307933 A1 10/2018 Iwaki
2018/0344150 A1* 12/2018 Bajraszewski ..... G01B 9/02091
2019/0099060 A1 4/2019 Yaguchi

FOREIGN PATENT DOCUMENTS

| WO | 2017073337 | 5/2017 |
|---|---|---|
| WO | 2017115442 | 7/2017 |
| WO | 2017212653 | 12/2017 |

OTHER PUBLICATIONS

Machine translation of WO 2017073337 (Year: 2024).*
(Continued)

*Primary Examiner* — James E Springer
(74) *Attorney, Agent, or Firm* — JCIPRNET

(57) ABSTRACT

The present invention is directed to providing an image processing apparatus and an image processing method that assist an observer of a time-series image in performing smooth observation while attracting attention of the observer. An image processing apparatus according to a first aspect of the present invention includes an image input unit that inputs a time-series image; an information acquiring unit that acquires information on a region of interest in the time-series image; a figure calculating unit that calculates a polygon or an ellipse surrounding the region of interest and having an area smaller than or equal to an area of a circumscribed rectangle, the circumscribed rectangle being a rectangle circumscribing the region of interest and formed of two sides parallel to a horizontal axis of the time-series image and other two sides parallel to a vertical axis of the time-series image; and a display control unit that causes a display apparatus to display a figure such that the figure is superimposed on the time-series image, the figure being based on the polygon or the ellipse and being disposed at sides or vertexes of the polygon or disposed on a circumference of the ellipse or at a plurality of positions on the circumference.

11 Claims, 13 Drawing Sheets

(51) Int. Cl.
  *G06V 10/143* (2022.01)
  *G06V 10/25* (2022.01)
  *G06V 10/44* (2022.01)
  *G06V 10/764* (2022.01)

(52) U.S. Cl.
  CPC ........ *A61B 1/00045* (2013.01); *A61B 1/0655* (2022.02); *G06V 10/143* (2022.01); *G06V 10/25* (2022.01); *G06V 10/454* (2022.01); *G06V 10/764* (2022.01)

(58) Field of Classification Search
  CPC .... G06V 10/25; G06V 10/454; G06V 10/143; G06V 10/764
  USPC .......................................................... 348/65
  See application file for complete search history.

(56) References Cited

OTHER PUBLICATIONS

"International Search Report (Form PCT/ISA/210) of PCT/JP2019/033598," mailed on Nov. 19, 2019, with English translation thereof, pp. 1-3.

"Written Opinion of the International Searching Authority (Form PCT/ISA/237) of PCT/JP2019/033598," mailed on Nov. 19, 2019, with English translation, pp. 1-9.

* cited by examiner

IMAGE PROCESSING APPARATUS AND IMAGE PROCESSING METHOD

CROSS-REFERENCE TO RELATED APPLICATIONS

The present application is a Continuation of PCT International Application No. PCT/JP2019/033598 filed on Aug. 28, 2019 claiming priority under 35 U.S.C § 119(a) to Japanese Patent Application No. 2018-177437 filed on Sep. 21, 2018. Each of the above applications is hereby expressly incorporated by reference, in its entirety, into the present application.

BACKGROUND OF THE INVENTION

1. Field of the Invention

The present invention relates to an image processing apparatus and an image processing method, and specifically relates to a technique of displaying a time-series image with a figure superimposed thereon.

2. Description of the Related Art

Regarding image processing apparatuses that acquire a time-series image, there has been known a technique of informing an observer of a region of interest or a candidate region of interest by superimposing a figure on the region. For example, WO2017/073337A describes displaying of a rectangular marker (bounding box) surrounding a candidate lesion region in an observation image of a subject acquired by an endoscope apparatus.

SUMMARY OF THE INVENTION

When a marker or the like is to be superimposed and displayed on an image, it is necessary to avoid hindering observation while attracting attention of an observer. In particular, in a case where a region of interest in a screen is a long and narrow ellipse and is tilted, for example, a large rectangle is generated and the most part thereof is not the region of interest, which hinders the observation. However, in the above-described related art described in WO2017/073337A, a rectangle surrounding a region of interest or the like is merely displayed, and no consideration is given to the shape, size, and so forth of the rectangle. Thus, displaying of a marker or the like may hinder the observation.

As described above, the related art does not assist an observer of a time-series image in performing smooth observation while attracting attention of the observer.

The present invention has been made in view of these circumstances, and an object of the present invention is to provide an image processing apparatus and an image processing method that assist an observer of a time-series image in performing smooth observation while attracting attention of the observer.

To achieve the above-described object, an image processing apparatus according to a first aspect of the present invention includes: an image input unit that inputs a time-series image; an information acquiring unit that acquires information on a region of interest in the time-series image; a figure calculating unit that calculates a polygon or an ellipse surrounding the region of interest and having an area smaller than or equal to an area of a circumscribed rectangle, the circumscribed rectangle being a rectangle circumscribing the region of interest and formed of two sides parallel to a horizontal axis of the time-series image and other two sides parallel to a vertical axis of the time-series image; and a display control unit that causes a display apparatus to display a figure such that the figure is superimposed on the time-series image, the figure being based on the polygon or the ellipse and being disposed at sides or vertexes of the polygon or disposed on a circumference of the ellipse or at a plurality of positions on the circumference.

In the first aspect, a figure is superimposed and displayed on a time-series image to attract attention of an observer. The figure that is superimposed and displayed is a figure based on a polygon or ellipse having an area smaller than or equal to the area of a circumscribed rectangle, and thus the portion other than the region of interest can be reduced and the degree of hindering observation can be reduced. This makes it possible to assist the observer of the time-series image in performing smooth observation while attracting attention of the observer. It is preferable to display a figure that does not overlap the region of interest so as not to hinder the observation.

In the first aspect, the type of image or photographic subject is not particularly limited. For example, a medical image, an image of a person or scenery, or the like may be used. The "ellipse" includes a circle (perfect circle).

In an image processing apparatus according to a second aspect, in the first aspect, the display control unit causes the display apparatus to display, as the figure, a figure disposed at the vertexes of the polygon and having a shape that varies according to interior angles of the vertexes. In the second aspect, a figure is disposed at the vertexes of a polygon so as not to hinder observation as much as possible. In the case of disposing a figure at the vertexes of a polygon, the shape is changed in accordance with the interior angles because the interior angles are not equal to each other depending on the type of polygon.

In an image processing apparatus according to a third aspect, in the first aspect, the display control unit causes the display apparatus to display, as the figure, a figure disposed at the vertexes of the polygon and having a size and/or a shape that is independent of interior angles of the vertexes. In the third aspect, a figure is disposed at the vertexes of a polygon so as not to hinder observation as much as possible.

In an image processing apparatus according to a fourth aspect, in any one of the first to third aspects, the display control unit causes the display apparatus to display, as the figure, a figure formed of the sides of the polygon or a part of the sides, or a figure formed of the circumference of the ellipse or a part of the circumference. In the fourth aspect, a figure formed of sides or a part of the sides, or a figure formed of a circumference or a part of the circumference is displayed so as not to hinder observation as much as possible. In the case of displaying a figure formed of a part of sides or a part of a circumference, the proportion of the "part" can be set in accordance with the degree of emphasizing or identifying the region of interest.

In an image processing apparatus according to a fifth aspect, in any one of the first to fourth aspects, the figure calculating unit sets, to the region of interest, a first axis and a second axis intersecting the first axis, and calculates, as the polygon, a quadrangle formed of two sides parallel to the first axis and two sides parallel to the second axis. The fifth aspect defines one aspect of a quadrangle calculation method. For example, the axis intersecting the region of interest over the largest length can be regarded as the first axis, and the axis intersecting the region of interest over the smallest length can be regarded as the second axis.

In an image processing apparatus according to a sixth aspect, in the fifth aspect, the figure calculating unit performs ellipse approximation on the region of interest and calculates a major axis and a minor axis of the ellipse, to calculate the polygon or the ellipse. In the case of calculating a polygon, a quadrangle as a polygon can be calculated by using one of the major axis and the minor axis as the first axis and the other as the second axis. Ellipse approximation is one aspect of an ellipse calculation method and is one aspect of a method for calculating two axes defining a polygon (quadrangle).

In an image processing apparatus according to a seventh aspect, in the fifth or sixth aspect, the figure calculating unit calculates a rectangle as the quadrangle. A rectangle is one aspect of a quadrangle.

In an image processing apparatus according to an eighth aspect, in any one of the first to seventh aspects, the image input unit inputs, as the time-series image, an image of a subject acquired by an endoscope apparatus. In the input time-series image, a lesion region, a candidate lesion region, or the like can be regarded as a region of interest.

In an image processing apparatus according to a ninth aspect, in any one of the first to eighth aspects, the information acquiring unit analyzes the time-series image to acquire the information on the region of interest. A machine learning algorithm may be used to analyze the time-series image.

In an image processing apparatus according to a tenth aspect, in any one of the first to ninth aspects, the image processing apparatus further includes a condition setting unit that sets, based on an instruction input by a user, the polygon or the ellipse to be calculated by the figure calculating unit and/or the figure to be displayed by the display control unit. According to the tenth aspect, the user is able to cause a figure to be calculated and/or displayed in desired conditions.

To achieve the above-described object, an image processing method according to an eleventh aspect of the present invention includes: an image input step of inputting a time-series image; an information acquisition step of acquiring information on a region of interest in the time-series image; a figure calculation step of calculating a polygon or an ellipse surrounding the region of interest and having an area smaller than or equal to an area of a circumscribed rectangle, the circumscribed rectangle being a rectangle circumscribing the region of interest and formed of two sides parallel to a horizontal axis of the time-series image and other two sides parallel to a vertical axis of the time-series image; and a display control step of causing a display apparatus to display a figure such that the figure is superimposed on the time-series image, the figure being based on the polygon or the ellipse and being disposed at sides or vertexes of the polygon or disposed on a circumference of the ellipse or at a plurality of positions on the circumference. According to the eleventh aspect, it is possible to assist the observer of the time-series image in performing smooth observation while attracting attention of the observer as in the first aspect. The image processing method according to the eleventh aspect may further include configurations similar to those according to the second to tenth aspects. In addition, a program that causes a computer to execute the image processing methods according to these aspects, and a non-transitory recording medium storing a computer-readable code of the program may be included in an aspect of the present invention. The "computer" for the program and the recording medium can be implemented by using one or more of various types of processors, such as a central processing unit (CPU).

As described above, the image processing apparatus and the image processing method according to the present invention are capable of assisting an observer of a time-series image in performing smooth observation while attracting attention of the observer.

DESCRIPTION OF THE PREFERRED EMBODIMENTS

Hereinafter, an embodiment of an image processing apparatus and an image processing method according to the present invention will be described in detail with reference to the attached drawings.

First Embodiment

Figure 1:
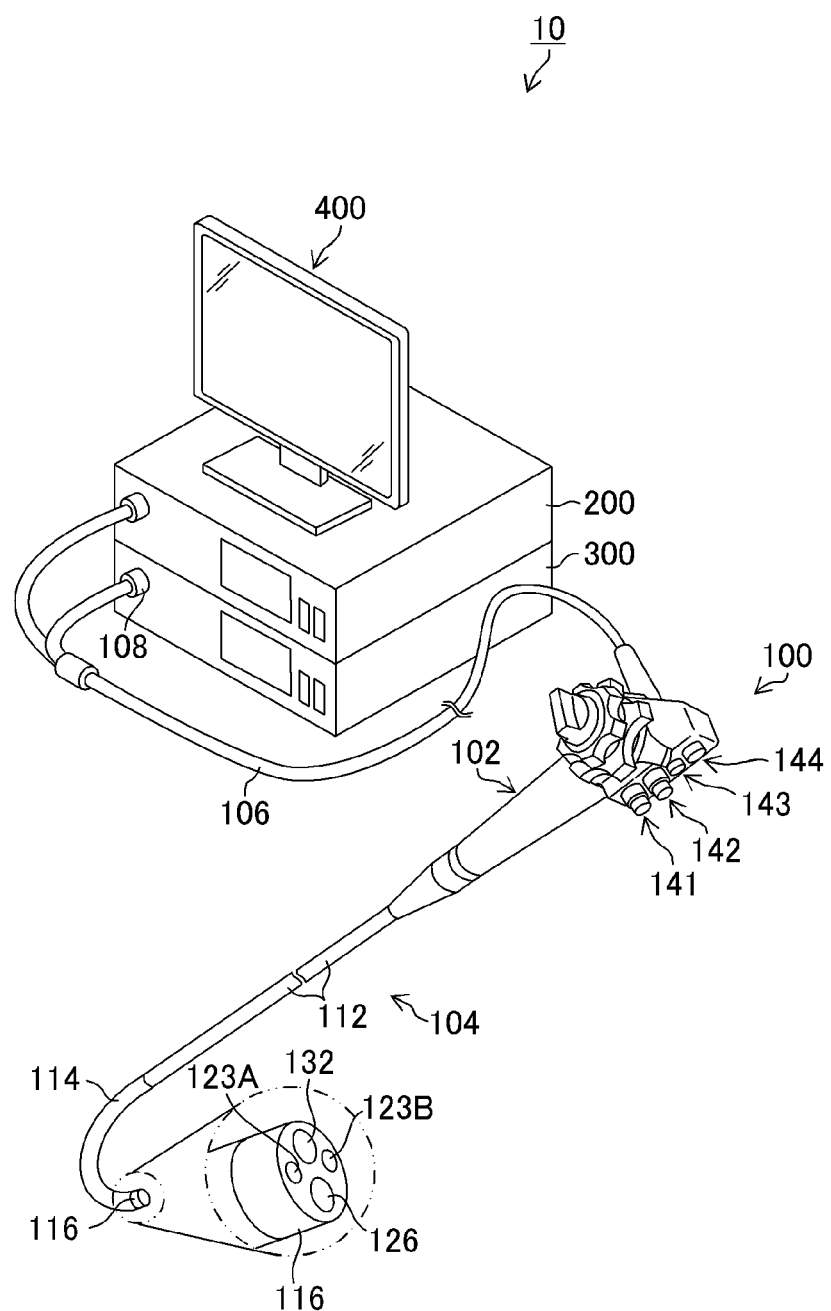
FIG. 1 is an external appearance diagram of an endoscope system according to a first embodiment.
Figure 2:
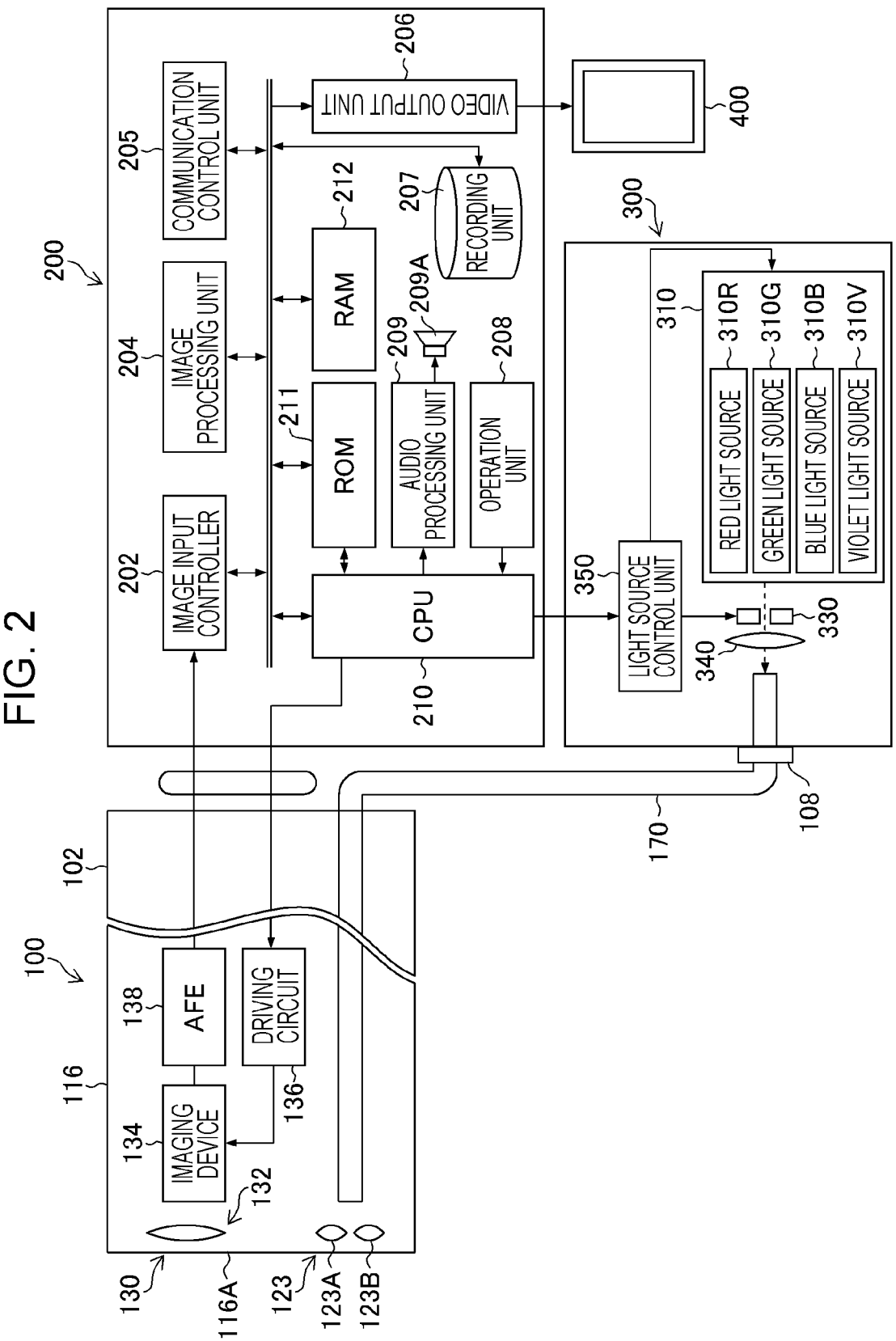
FIG. 2 is a block diagram illustrating the configuration of a main part of the endoscope system.

FIG. 1 is an external appearance diagram illustrating an endoscope system 10 (an endoscope apparatus, an image processing apparatus, a diagnosis assistance apparatus, an endoscope system, a medical image processing apparatus) according to a first embodiment, and FIG. 2 is a block diagram illustrating the configuration of a main part of the endoscope system 10. As illustrated in FIGS. 1 and 2, the endoscope system 10 is constituted by an endoscope main body 100 (an endoscope apparatus), a processor 200 (a processor, an image processing apparatus, a medical image processing apparatus), a light source apparatus 300 (a light source apparatus), and a monitor 400 (a display apparatus).

Configuration of Endoscope Main Body

The endoscope main body 100 includes a handheld operation section 102 (a handheld operation section) and an insertion section 104 (an insertion section) that communicates with the handheld operation section 102. An operator (a user) operates the handheld operation section 102 while grasping it and inserts the insertion section 104 into a body of a subject (a living body) to perform observation. The handheld operation section 102 is provided with an air/water supply button 141, a suction button 142, a function button 143 to which various functions are allocated, and an imaging button 144 for receiving an imaging instruction operation (a still image, a moving image). The insertion section 104 is constituted by a soft part 112 (a soft part), a bending part 114 (a bending part), and a tip rigid part 116 (a tip rigid part), which are arranged in this order from the handheld operation section 102 side. That is, the bending part 114 is connected to a base end side of the tip rigid part 116, and the soft part 112 is connected to a base end side of the bending part 114. The handheld operation section 102 is connected to a base end side of the insertion section 104. The user is able to change the orientation of the tip rigid part 116 in an up, down, left, or right direction by causing the bending part 114 to bend by operating the handheld operation section 102. The tip rigid part 116 is provided with an imaging optical system 130 (an imaging unit), an illumination unit 123, a forceps port 126, and so forth (see FIG. 1 to FIG. 2).

During observation or treatment, an operation of an operation unit 208 (see FIG. 2) enables white light and/or narrow-band light (one or more of red narrow-band light, green narrow-band light, blue narrow-band light, and violet narrow-band light) to be radiated from illumination lenses 123A and 123B of the illumination unit 123. In addition, an operation of the air/water supply button 141 enables washing water to be ejected from a water supply nozzle that is not illustrated, so that an imaging lens 132 (an imaging lens, an imaging unit) of the imaging optical system 130 and the illumination lenses 123A and 123B can be washed. The forceps port 126 opening in the tip rigid part 116 communicates with a pipe line that is not illustrated, so that a treatment tool that is not illustrated and is for extirpating a tumor or the like can be inserted into the pipe line and necessary treatment can be given to a subject by moving the treatment tool forward or backward as appropriate.

As illustrated in FIG. 1 and FIG. 2, the imaging lens 132 (an imaging unit) is disposed on a distal-end-side surface 116A of the tip rigid part 116. An imaging device 134 (an imaging device, an imaging unit) of a complementary metal-oxide semiconductor (CMOS) type, a driving circuit 136, and an analog front end (AFE) 138 are disposed behind the imaging lens 132, and these elements output an image signal. The imaging device 134 is a color imaging device and includes a plurality of pixels constituted by a plurality of light-receiving elements arranged in a matrix (arranged two-dimensionally) in a specific pattern arrangement (Bayer arrangement, X-Trans (registered trademark) arrangement, honeycomb arrangement, or the like). Each pixel of the imaging device 134 includes a microlens, a red (R), green (G), or blue (B) color filter, and a photoelectric conversion unit (a photodiode or the like). The imaging optical system 130 is capable of generating a color image from pixel signals of three colors, red, green, and blue, and is also capable of generating an image from pixel signals of any one or two colors among red, green, and blue. In the first embodiment, a description will be given of a case where the imaging device 134 is a CMOS-type imaging device, but the imaging device 134 may be of a charge coupled device (CCD) type. Each pixel of the imaging device 134 may further include a violet color filter corresponding to a violet light source and/or an infrared filter corresponding to an infrared light source.

An optical image of a subject (a tumor portion, a lesion portion) is formed on a light-receiving surface (an imaging surface) of the imaging device 134 by the imaging lens 132, converted into an electric signal, output to the processor 200 through a signal cable that is not illustrated, and converted into a video signal. Accordingly, an observation image is displayed on the monitor 400, which is connected to the processor 200.

The illumination lenses 123A and 123B of the illumination unit 123 are provided next to the imaging lens 132 on the distal-end-side surface 116A of the tip rigid part 116. An emission end of a light guide 170, which will be described below, is disposed behind the illumination lenses 123A and 123B. The light guide 170 extends through the insertion section 104, the handheld operation section 102, and a universal cable 106, and an incidence end of the light guide 170 is located in a light guide connector 108.

Configuration of Light Source Apparatus

As illustrated in FIG. 2, the light source apparatus 300 is constituted by a light source 310 for illumination, a diaphragm 330, a condenser lens 340, a light source control unit 350, and so forth, and causes observation light to enter the light guide 170. The light source 310 includes a red light source 310R, a green light source 310G, a blue light source 310B, and a violet light source 310V that radiate red narrow-band light, green narrow-band light, blue narrow-band light, and violet narrow-band light, respectively, and is capable of radiating red narrow-band light, green narrow-band light, blue narrow-band light, and violet narrow-band light. The illuminance of observation light from the light source 310 is controlled by the light source control unit 350, which is capable of decreasing the illuminance of observation light or stopping illumination as necessary.

The light source 310 is capable of emitting red narrow-band light, green narrow-band light, blue narrow-band light, and violet narrow-band light in any combination. For example, the light source 310 is capable of simultaneously emitting red narrow-band light, green narrow-band light, blue narrow-band light, and violet narrow-band light to radiate white light (normal light) as observation light, and is also capable of emitting any one or two of red narrow-band light, green narrow-band light, blue narrow-band light, and violet narrow-band light to radiate narrow-band light (special light). The light source 310 may further include an infrared light source that radiates infrared light (an example of narrow-band light). Alternatively, with use of a light source that radiates white light and a filter that allows white light and each narrow-band light to pass therethrough, white light or narrow-band light may be radiated as observation light.

Wavelength Range of Light Source

The light source 310 may be a light source that generates light in a white range or light in a plurality of wavelength ranges as the light in the white range, or may be a light source that generates light in a specific wavelength range narrower than the white wavelength range. The specific wavelength range may be a blue range or green range in a visible range, or may be a red range in the visible range. In a case where the specific wavelength range is the blue range or green range in the visible range, the specific wavelength range may include a wavelength range of 390 nm or more and 450 nm or less or a wavelength range of 530 nm or more and 550 nm or less, and the light in the specific wavelength range may have a peak wavelength in the wavelength range of 390 nm or more and 450 nm or less or the wavelength range of 530 nm or more and 550 nm or less. In a case where the specific wavelength range is the red range in the visible range, the specific wavelength range may include a wavelength range of 585 nm or more and 615 nm or less or a wavelength range of 610 nm or more and 730 nm or less, and the light in the specific wavelength range may have a peak wavelength in the wavelength range of 585 nm or more and 615 nm or less or the wavelength range of 610 nm or more and 730 nm or less.

The above-described specific wavelength range may include a wavelength range in which a light absorption coefficient is different between oxyhemoglobin and deoxyhemoglobin, and the light in the specific wavelength range may have a peak wavelength in the wavelength range in which the light absorption coefficient is different between oxyhemoglobin and deoxyhemoglobin. In this case, the specific wavelength range may include a wavelength range of 400±10 nm, a wavelength range of 440±10 nm, a wavelength range of 470±10 nm, or a wavelength range of 600 nm or more and 750 nm or less, and the light in the specific wavelength range may have a peak wavelength in the wavelength range of 400±10 nm, the wavelength range of 440±10 nm, the wavelength range of 470±10 nm, or the wavelength range of 600 nm or more and 750 nm or less.

The wavelength range of the light generated by the light source 310 may include a wavelength range of 790 nm or more and 820 nm or less or a wavelength range of 905 nm or more and 970 nm or less, and the light generated by the light source 310 may have a peak wavelength in the wavelength range of 790 nm or more and 820 nm or less or the wavelength range of 905 nm or more and 970 nm or less.

Alternatively, the light source 310 may include a light source that radiates excitation light whose peak is 390 nm or more and 470 nm or less. In this case, a medical image (an inside-of-living-body image) having information about fluorescence emitted by a fluorescent substance in a subject (a living body) can be acquired. In the case of acquiring a fluorescence image, a pigment for a fluorescence method may be used.

It is preferable that the type of the light source 310 (a laser light source, a xenon light source, a light-emitting diode (LED) light source, or the like), the wavelength of the light source 310, the presence or absence of a filter for the light source 310, and so forth be determined in accordance with the type of photographic subject, the purpose of observation, or the like. It is also preferable that, during observation, the wavelengths of observation light be combined and/or switched in accordance with the type of photographic subject, the purpose of observation, or the like. In the case of switching the wavelength, for example, a disc-shaped filter (a rotary color filter) that is disposed in front of the light source and that is provided with a filter for transmitting or blocking light of a specific wavelength may be rotated to switch the wavelength of light to be radiated.

The imaging device used to carry out the present invention is not limited to a color imaging device in which color filters are disposed for the individual pixels, such as the imaging device 134, and may be a monochrome imaging device. In the case of using a monochrome imaging device, imaging can be performed in a frame sequential (color sequential) manner by sequentially switching the wavelength of observation light. For example, the wavelength of outgoing observation light may be sequentially switched among blue, green, and red, or wide-band light (white light) may be radiated and the wavelength of outgoing observation light may be switched by using a rotary color filter (red, green, blue, and the like). Alternatively, one or a plurality of types of narrow-band light (green, blue, and the like) may be radiated and the wavelength of outgoing observation light may be switched by using a rotary color filter (green, blue, and the like). The narrow-band light may be infrared light of two or more different wavelengths (first narrow-band light and second narrow-band light).

As a result of connecting the light guide connector 108 (see FIG. 1) to the light source apparatus 300, observation light radiated by the light source apparatus 300 is transmitted through the light guide 170 to the illumination lenses 123A and 123B and is radiated from the illumination lenses 123A and 123B to an observation range.

Configuration of Processor

The configuration of the processor 200 will be described with reference to FIG. 2. In the processor 200, an image input controller 202 receives an image signal output from the endoscope main body 100, an image processing unit 204 performs necessary image processing thereon, and a video output unit 206 outputs a resulting image signal. Accordingly, an observation image (an inside-of-living-body image) is displayed on the monitor 400 (a display apparatus). These processing operations are performed under control by a central processing unit (CPU) 210. Specifically, the CPU 210 has functions as an image input unit, an information acquiring unit, a figure calculating unit, a display control unit, and a condition setting unit. A communication control unit 205 controls communication with a hospital information system (HIS), a hospital local area network (LAN), and the like that are not illustrated. In a recording unit 207, an image of a photographic subject (a medical image, a captured image), information indicating a result of detection and/or classification of a region of interest, and the like are recorded. An audio processing unit 209 outputs a message (sound) or the like based on the result of detection and/or classification of the region of interest from a speaker 209A under control by the CPU 210 and the image processing unit 204.

A read only memory (ROM) 211 is a nonvolatile storage element (a non-transitory recording medium) and stores a computer-readable code of a program that causes the CPU 210 and/or the image processing unit 204 (an image processing apparatus, a computer) to execute the image processing method according to the present invention. A random access memory (RAM) 212 is a storage element for temporary storage in various processing operations and can be used as a buffer when acquiring an image.

Functions of Image Processing Unit

Figure 3:
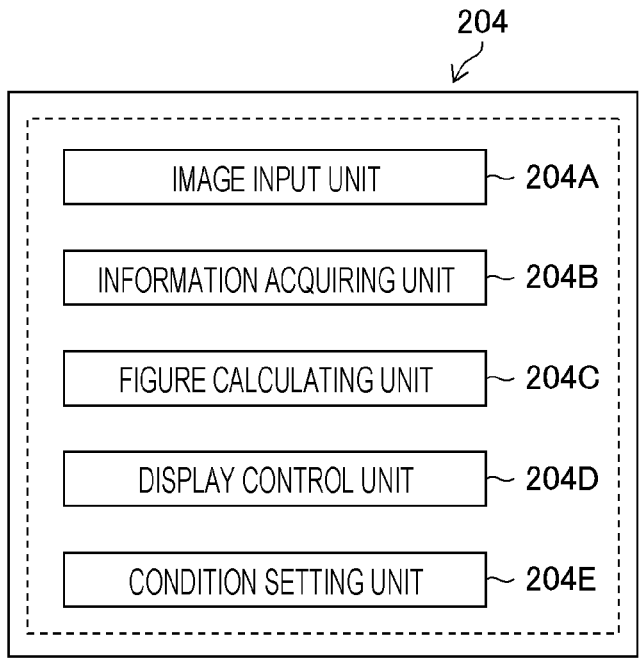
FIG. 3 is a diagram illustrating a functional configuration of an image processing unit.

FIG. 3 is a diagram illustrating a functional configuration of the image processing unit 204 (a medical image acquiring unit, a medical image analysis processing unit, a medical image analysis result acquiring unit). The image processing unit 204 has an image input unit 204A (an image input unit), an information acquiring unit 204B (an information acquiring unit), a figure calculating unit 204C (a figure calculating unit), a display control unit 204D (a display control unit), and a condition setting unit 204E (a condition setting unit). The information acquiring unit 204B also operates as a medical image analysis processing unit.

In addition, the image processing unit 204 may include a special-light image acquiring unit that acquires a special-light image having information about a specific wavelength range on the basis of a normal-light image that is acquired by radiating light in the white range or light in a plurality of wavelength ranges as the light in the white range. In this case, a signal in the specific wavelength range can be acquired through computation based on color information of RGB (R: red, G: green, B: blue) or CMY (C: cyan, M: magenta, Y: yellow) included in the normal-light image.

In addition, the image processing unit 204 may include a feature quantity image generating unit that generates a feature quantity image through computation based on at least one of a normal-light image that is acquired by radiating light in the white range or light in a plurality of wavelength ranges as the light in the white range or a special-light image that is acquired by radiating light in a specific wavelength range, and may acquire and display the feature quantity image as a medical image. The information acquiring unit 204B may have a function of a feature-quantity-image generating unit.

The processing operations using these functions of the image processing unit 204 will be described in detail below. The processing operations using these functions are performed under control by the CPU 210.

The above-described functions of the image processing unit 204 can be implemented by using various types of processors. The various types of processors include, for example, a central processing unit (CPU) which is a general-purpose processor that executes software (program) to implement various functions. Also, the various types of processors include a graphics processing unit (GPU) which is a processor dedicated to image processing, and a programmable logic device (PLD) which is a processor whose circuit configuration is changeable after manufacturing, such as a field programmable gate array (FPGA). Furthermore, the various types of processors include a dedicated electric circuit which is a processor having a circuit configuration designed exclusively for executing specific processing, such as an application specific integrated circuit (ASIC).

The function of each unit may be implemented by one processor or may be implemented by a plurality of processors of the same type or different types (for example, a combination of a plurality of FPGAs, a combination of a CPU and an FPGA, or a combination of a CPU and a GPU). A plurality of functions may be implemented by one processor. A first example of implementing a plurality of functions by one processor is that a combination of one or more CPUs and software constitute one processor and the one processor implements the plurality of functions, as represented by a computer, such as a main body of an image processing apparatus or a server. A second example is that a processor that implements the functions of an entire system by one integrated circuit (IC) chip is used, as represented by a system on chip (SoC). In this way, various functions are configured as a hardware structure by using one or more of the above-described various types of processors. Furthermore, the hardware structure of the various types of processors is, more specifically, electric circuitry formed by combining circuit elements such as semiconductor elements. The electric circuitry may be electric circuitry that implements the above-described functions by using logical disjunction, logical conjunction, logical negation, exclusive disjunction, and logical operation combining them.

When the above-described processor or electric circuitry executes the software (program), a processor (computer)-readable code of the software to be executed is stored in a non-transitory recording medium, such as a read only memory (ROM), and the processor refers to the software. The software stored in the non-transitory recording medium includes a program for executing input, analysis, display control, and so forth of an image. The code may be recorded on a non-transitory recording medium, such as a magneto-optical recording device of various types or a semiconductor memory, instead of the ROM. In the processing using the software, a random access memory (RAM) may be used as a transitory storage region, for example, and data stored in an electrically erasable and programmable read only memory (EEPROM) that is not illustrated can be referred to, for example.

Configuration of Operation Unit

The processor 200 includes the operation unit 208. The operation unit 208 includes an operation mode setting switch or the like that is not illustrated and is capable of setting the wavelength of observation light (white light or narrow-band light, which narrow-band light is to be used in the case of narrow-band light). In addition, the operation unit 208 includes a keyboard and a mouse that are not illustrated. A user is able to perform operations of setting an imaging condition and a display condition, or provide an instruction to capture a moving image or a still image (an acquisition instruction) via these devices (the instruction to capture a moving image or a still image may be provided using the imaging button 144). These setting operations may be performed via a foot switch that is not illustrated, or may be performed by using a voice, a line of sight, a gesture, or the like.

Configuration of Recording Unit

The rescoring unit 207 (a recording device) is configured including a non-transitory recording medium, such as a magneto-optical recording medium of various types or a semiconductor memory, and a control unit for the recording medium, and stores an input time-series image, information on a region of interest about the time-series image, information on a figure to be superimposed on an image, and so forth in association with each other. These images and information are displayed on the monitor 400 as a result of an operation performed via the operation unit 208 and control by the CPU 210 and/or the image processing unit 204.

In addition to the above-described images, an analysis result about either or both of a region of interest (a region of concern), which is a region to be focused on included in a medical image, and the presence or absence of a target to be focused on may be recorded in the recording unit 207 (a recording device). In this case, the image processing unit 204 (a medical image analysis processing unit, a medical image analysis result acquiring unit) is capable of acquiring the analysis result from the recording unit 207 and displaying the analysis result on the monitor 400.

Configuration of Display Apparatus

The monitor 400 (a display apparatus) displays an input time-series image, information on a region of interest about the time-series image, a figure to be superimposed on an image, and so forth, as a result of an operation performed via the operation unit 208 and control by the CPU 210 and/or the image processing unit 204. The monitor 400 has a touch panel that is not illustrated and that is for performing an imaging condition setting operation and/or a display condition setting operation.

Image Processing Method

Figure 4:
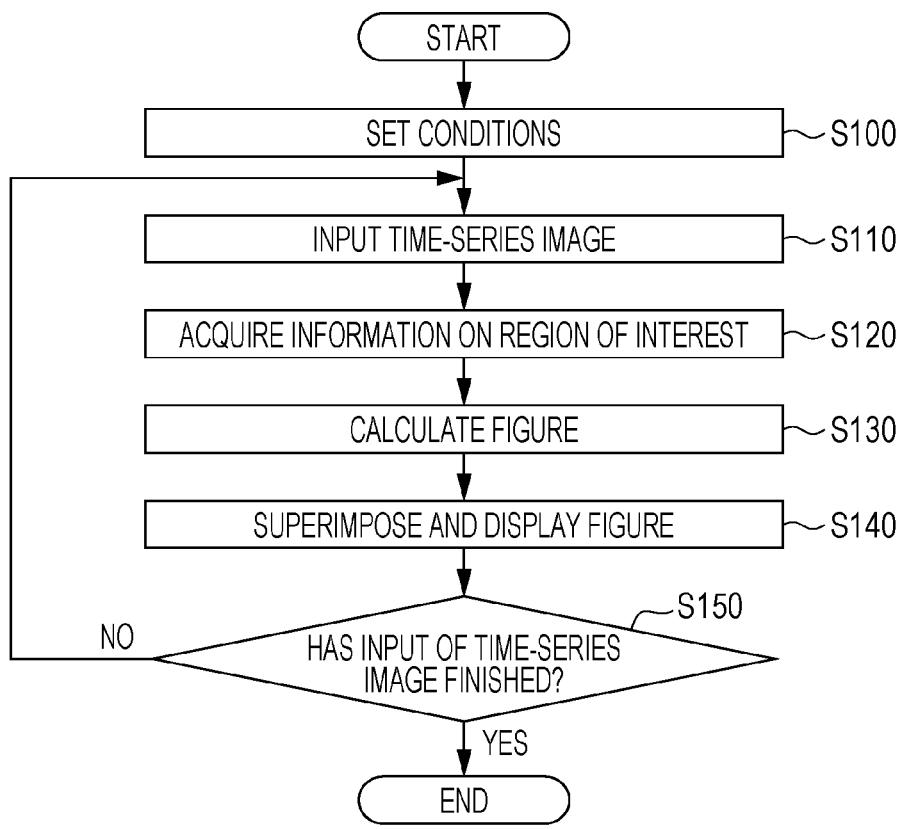
FIG. 4 is a flowchart illustrating the process of an image processing method according to the first embodiment.

An image processing method using the endoscope system 10 having the above-described configuration will be described. FIG. 4 is a flowchart illustrating the procedure of an image processing method according to the first embodiment.

Setting of Conditions

Figure 5:
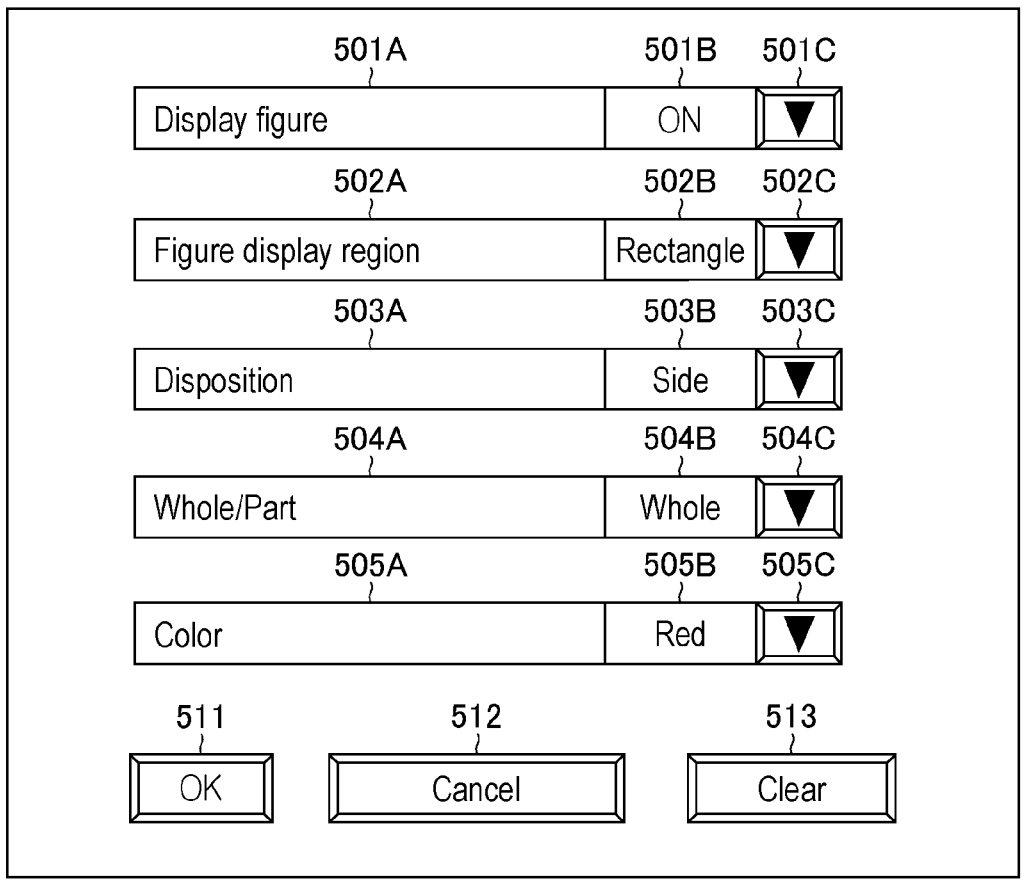
FIG. 5 is a diagram illustrating an example of a display condition setting screen.

The condition setting unit 204E sets a polygon or ellipse to be calculated by the figure calculating unit 204C and or a figure to be displayed by the display control unit 204D, on the basis of an instruction input by a user via the operation unit 208 (step S100: a condition setting step). FIG. 5 illustrates an example of a condition setting screen (a screen that allows a user to input an instruction). FIG. 5 illustrates condition names (regions 501A to 505A), details of set conditions (regions 501B to 505B), and buttons 501C to 505C for setting conditions for individual items of settable conditions. At the lower portion of the screen, there are provided a button 511 for confirming display conditions, a button 512 for cancelling change of conditions, and a button 513 for clearing change of conditions (returning to initial values). The screen in FIG. 5 is displayed on the monitor 400. The conditions can be set by a user's operation performed via a touch panel of the monitor 400 and/or the keyboard and mouse (not illustrated) of the operation unit 208. The setting of conditions may be performed not only before the start of processing but also during or after execution of the flowchart in FIG. 4 when necessary. The layout and items of the condition setting screen described below are an example of setting of conditions, and another style can be employed as necessary.

Figure 6:
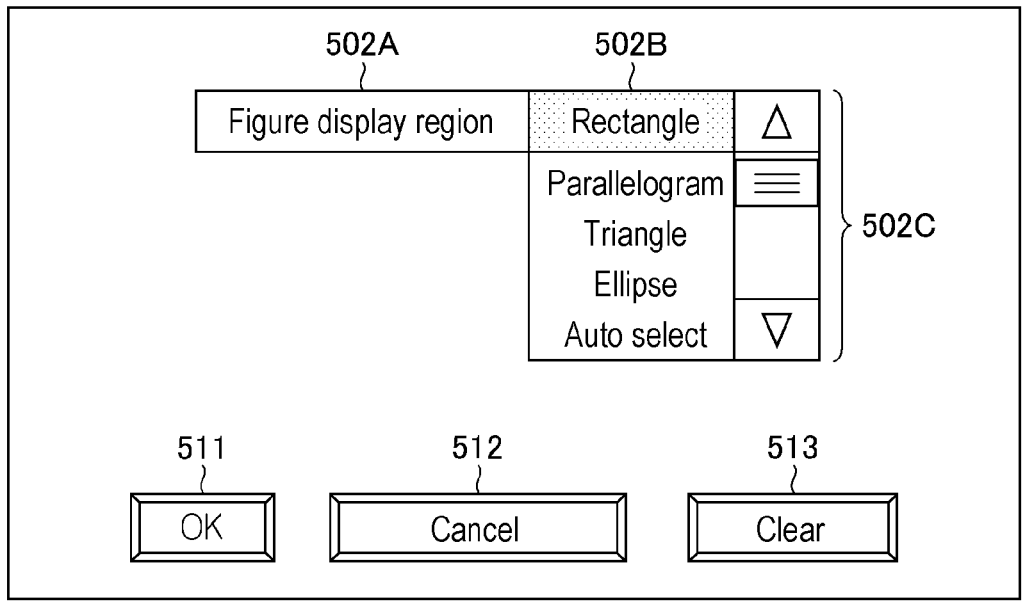
FIG. 6 is a diagram illustrating another example of the display condition setting screen.

FIG. 6 is a diagram illustrating a state of setting a figure display region (the shape of the region where a figure is to be disposed; polygon or ellipse) among the items illustrated in FIG. 5 (illustration of the other conditions is omitted). When the button 502C is designated on the screen in FIG. 5, selectable conditions are displayed in a pull-down menu as in the example in FIG. 6. In the example in FIG. 6, the user is able to select, as a figure display region, rectangle, parallelogram, triangle, ellipse, or auto select by operating the button 502C. In the case of "auto select", the endoscope system 10 selects any one of rectangle, parallelogram, triangle, and ellipse in accordance with the shape, size, and the like of a region of interest. In a case where the monitor 400 is constituted by a touch panel, an instruction operation of the user may be received via the touch panel. In the endoscope system 10 according to the first embodiment, the user is able to set desired conditions via such a screen.

Input of Time-Series Image and Acquisition of Information on Region of Interest

The image input unit 204A inputs a time-series image of a subject acquired by the endoscope system 10 (an endoscope apparatus) (step S110: an image input step). The information acquiring unit 204B acquires information (the position, size, shape, and so forth of a region of interest) on the region of interest (also referred to as a region of concern) about individual frames constituting the time-series image (step S120: an information acquisition step). Information acquired in advance may be acquired, or the input time-series image may be analyzed and a region of interest may be detected.

Detection of Region of Interest by CAD System

Detection of a region of interest can be performed when the information acquiring unit 204B includes, for example, a computer aided diagnosis (CAD) system. Specifically, for example, on the basis of a feature quantity of pixels of a medical image, the presence or absence of a region of interest (a region of interest which is a region to be focused on) and a target (a target to be focused on) in the region of interest can be extracted. In this case, the information acquiring unit 204B divides a detection target image into, for example, a plurality of rectangular regions, and sets the individual rectangular regions obtained through the division as local regions. The information acquiring unit 204B calculates, for each local region of the detection target image, the feature quantity (for example, a hue) of pixels in the local region, and determines a local region having a specific hue among the individual local regions to be a region of interest.

Detection of Region of Interest by Machine Learning

Detection of a region of interest may be performed by using a learner (a learned model) constructed through machine learning. For example, every time a new image is recorded in the recording unit 207 (or every time a new image is captured), the information acquiring unit 204B performs image analysis processing on the basis of a machine learning algorithm and thereby analyzes whether or not each frame of a time-series image includes a region of interest. The machine learning algorithm to be used may be, for example, the method of a convolutional neural network, that is, an algorithm of recognizing whether or not an image includes a region of interest by using an input layer, an intermediate layer (repetition of convolutional layers and pooling layers; it is preferable to have a fully connected layer in the case of discriminating a region of interest), and an output layer. In the case of performing segmentation on a region of interest, the output layer grasps, in units of pixels, the position of the region of interest depicted in an image by using a "feature map" acquired from the intermediate layer. That is, it is possible to detect, for each pixel of an endoscopic image, whether or not the pixel belongs to the region of interest, and to output a detection result. On the other hand, in the case of performing object detection, determination in units of pixels is not necessary, and the output layer outputs position information on the target. Image analysis processing using machine learning may use a learner generated by giving images labeled with "is a region of interest" or "is not a region of interest" as training data. "Whether or not to perform such machine learning" and/or "whether or not to use a learning result" may be set in accordance with a user operation via the operation unit 208 and the monitor 400.

Examples of a region of interest for which information is acquired in step S120 may include a polyp, a cancer, a colon diverticulum, an inflammation, a treatment scar (a scar of endoscopic mucosal resection (EMR), a scar of endoscopic submucosal dissection (ESD), a clip portion, or the like), a bleeding point, a perforation, angiodysplasia, and the like.

Figure to be Superimposed and Displayed

Figure 7:
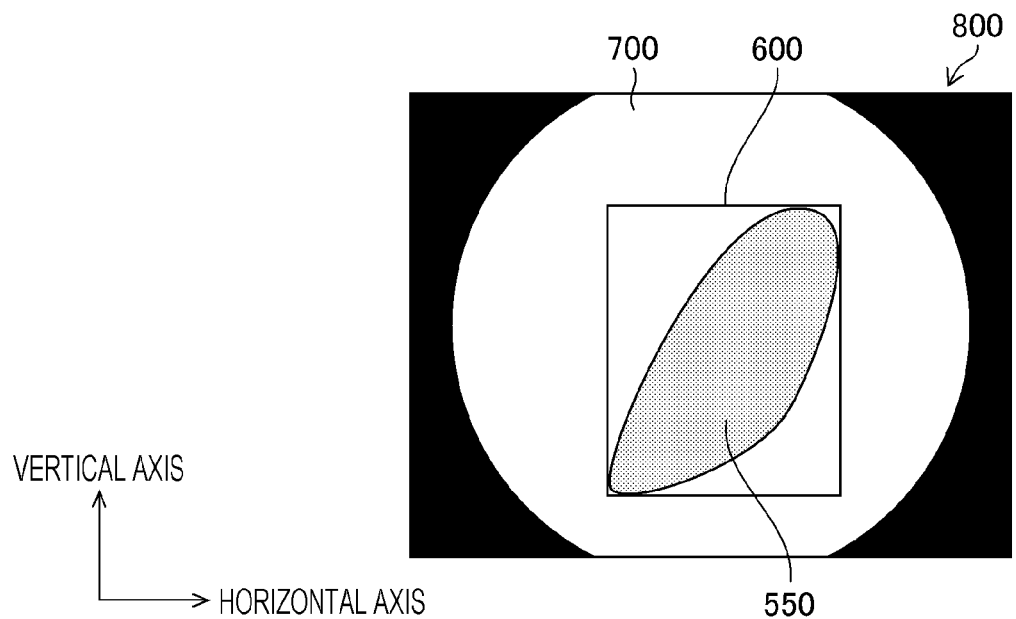
FIG. 7 is a diagram illustrating an example of a circumscribed rectangle for a region of interest.

In the case of superimposing and displaying a figure on an image, if a circumscribed rectangle 600 (a rectangle circumscribing a region of interest 550 and formed of two sides parallel to the horizontal axis of a time-series image 800 and the other two sides parallel to the vertical axis of the time-series image 800) or a figure larger than the circumscribed rectangle 600 is superimposed as is on an image as illustrated in FIG. 7, the portion other than the region of interest 550 (the upper-left portion and the lower-right portion) is large and hinders observation. Accordingly, in the endoscope system 10 according to the first embodiment, a figure based on "a polygon or ellipse surrounding the region of interest and having an area smaller than or equal to the area of the circumscribed rectangle" is calculated as a figure to be superimposed and displayed on the image (step S130: a figure calculation step), and is superimposed and displayed (step S140: a display control step). A region 700 in FIG. 7 represents the field of view of the endoscope (almost circular because the imaging angle of view is large) (the same applies to the following figures).

Calculation of Polygon or Ellipse Surrounding Region of Interest

Figure 8A:
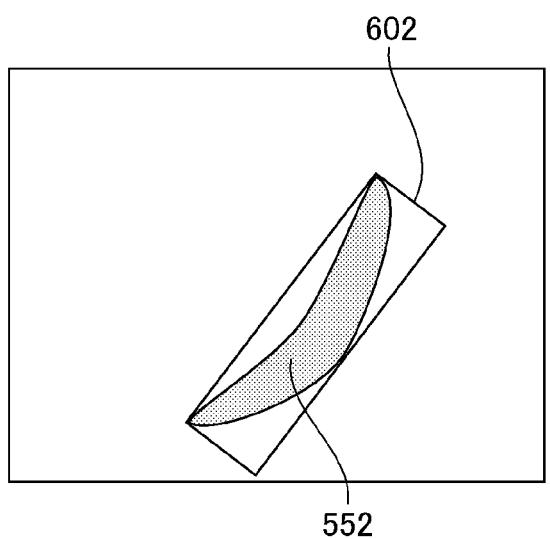
FIGS. 8A and 8B are diagrams illustrating an example of figures of a rectangle and a parallelogram, respectively.
Figure 8B:
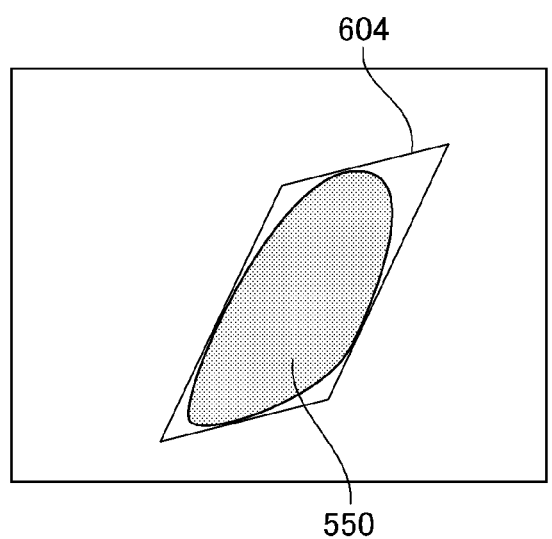

The figure calculating unit 204C calculates a polygon or ellipse surrounding the region of interest and having an area smaller than or equal to the area of the circumscribed rectangle (step S130: a figure calculation step). The figure calculating unit 204C may calculate a polygon or ellipse having an area smaller than the area of the circumscribed rectangle. The calculation is performed in accordance with the conditions set in step S100. The polygon or ellipse to be calculated may be tilted with respect to the horizontal axis or the vertical axis. In the case of calculating a quadrangle as a polygon, a rectangle (an oblong rectangle) may be calculated or a parallelogram may be calculated. For example, a tilted rectangle 602 surrounding a region of interest 552 may be calculated as illustrated in FIG. 8A, or a tilted parallelogram 604 surrounding the region of interest 550 may be calculated as illustrated in FIG. 8B. To avoid hindering observation, it is preferable to calculate a polygon or ellipse that does not overlap the region of interest.

Calculation of Polygon and Setting of Axes

Figure 9A:
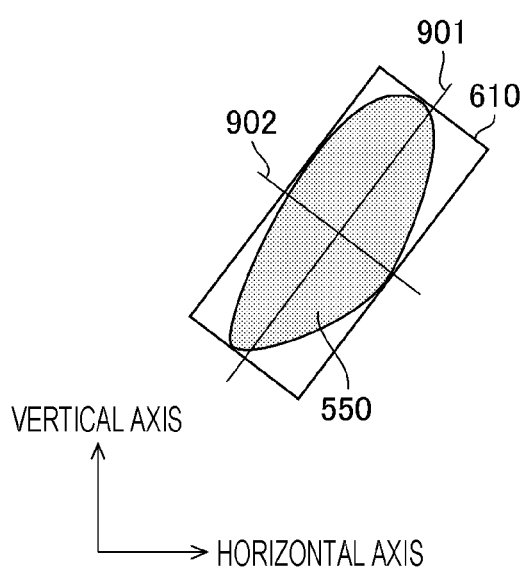
FIGS. 9A and 9B are diagrams illustrating examples of setting a first axis and a second axis.
Figure 9B:
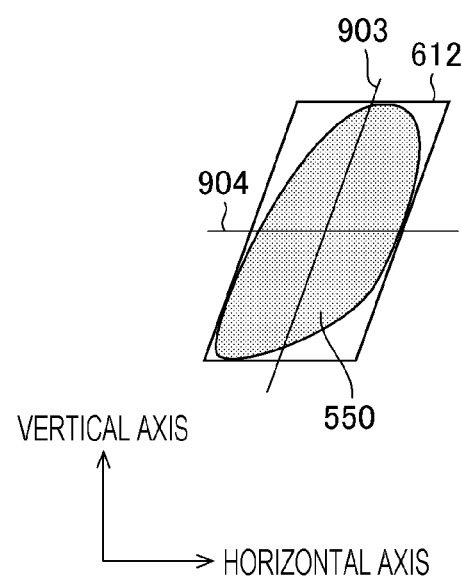

In the case of calculating a polygon in step S130, the figure calculating unit 204C sets, to the region of interest, a first axis and a second axis intersecting the first axis, and calculates, as a polygon, a quadrangle formed of two sides parallel to the first axis and two sides parallel to the second axis (step S130: a figure calculation step). The first axis and the second axis can be set in various directions, for example, the first axis or the second axis is set in the horizontal direction or the vertical direction, or the first axis and/or the second axis is set in the direction in which the length over which the axis crosses the region of interest is maximum or minimum. FIGS. 9A and 9B are diagrams illustrating setting examples of the first axis and the second axis. FIG. 9A illustrates a state in which a first axis 901 (a first axis) and a second axis 902 (a second axis) orthogonal to the first axis 901 are set to the region of interest 550, and a rectangle 610 (a polygon, a quadrangle, a rectangle) formed of two sides parallel to the first axis 901 and two sides parallel to the second axis 902 is calculated. On the other hand, FIG. 9B illustrates a state in which a first axis 903 (a first axis) and a second axis 904 (a second axis) are set to the region of interest 550, and a parallelogram 612 (a polygon, a quadrangle, a parallelogram) formed of two sides parallel to the first axis 903 and two sides parallel to the second axis 904 is calculated.

Calculation of Ellipse and Polygon by Ellipse Approximation

Figure 10:
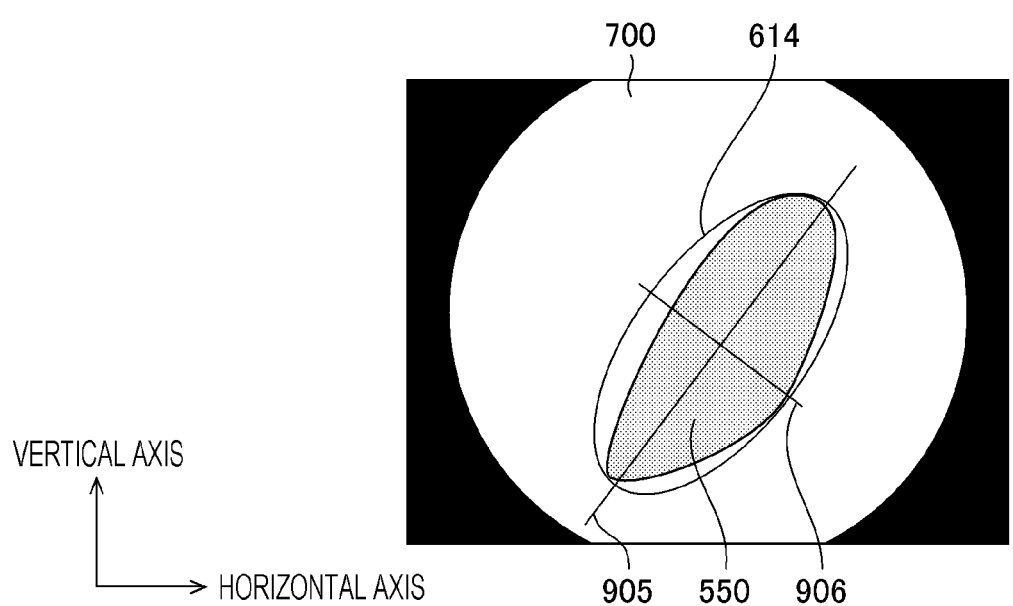
FIG. 10 is a diagram illustrating a state of calculating an ellipse.

In step S130, the figure calculating unit 204C is capable of calculating an ellipse or a polygon (quadrangle) by performing ellipse approximation on the region of interest and calculating the major axis and minor axis of the ellipse (step S130: a figure calculation step). For example, as illustrated in FIG. 10, the figure calculating unit 204C is callable of calculating, for the region of interest 550, an ellipse 614 having a major axis 905 (a major axis) and a minor axis 906 (a minor axis) orthogonal to the major axis 905. As in the case of calculating a polygon, the major axis and the minor axis can be set in various directions, for example, one of them is set in the horizontal direction or the vertical direction, or set in the direction in which the length over which the axis crosses the region of interest is maximum or minimum. As in the case of calculating a polygon, it is preferable to calculate an ellipse that does not overlap the region of interest. In addition, the figure calculating unit 204C may regard one of the major axis and minor axis calculated in this manner as a first axis and the other as a second axis, and may calculate as a polygon a quadrangle formed of two sides parallel to the first axis and two sides parallel to the second axis. The ellipse approximation is one aspect of an ellipse calculation method and is also an aspect of a method for calculating two axes defining a polygon (a quadrangle).

Superimposition and Display of Figure

The display control unit 204D superimposes a figure based on the polygon or ellipse calculated by the figure calculating unit 204C on a time-series image and causes the monitor 400 (a display apparatus) to display the figure (step S140: a display control step). Specifically, a figure disposed at the sides or vertexes of the calculated polygon is displayed, or a figure disposed on the circumference of the ellipse or at a plurality of positions on the circumference is displayed. Hereinafter, examples of a figure to be superimposed and displayed will be described.

EXAMPLES OF FIGURE TO BE SUPERIMPOSED AND DISPLAYED

Example 1

Figure 11A:
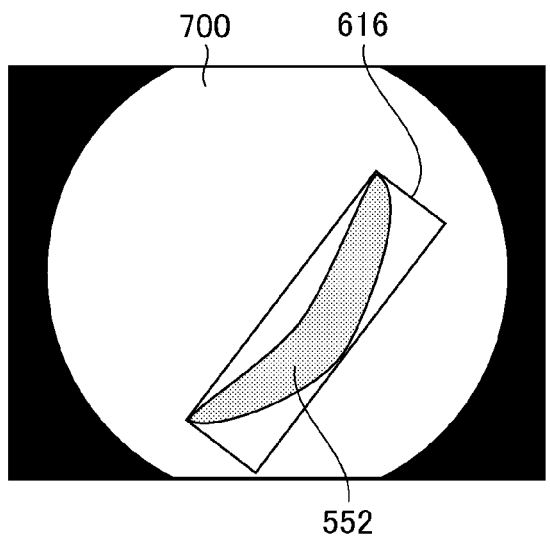
FIGS. 11A and 11B are diagrams illustrating states in which a figure is disposed at the sides and vertexes of a rectangle.
Figure 11B:
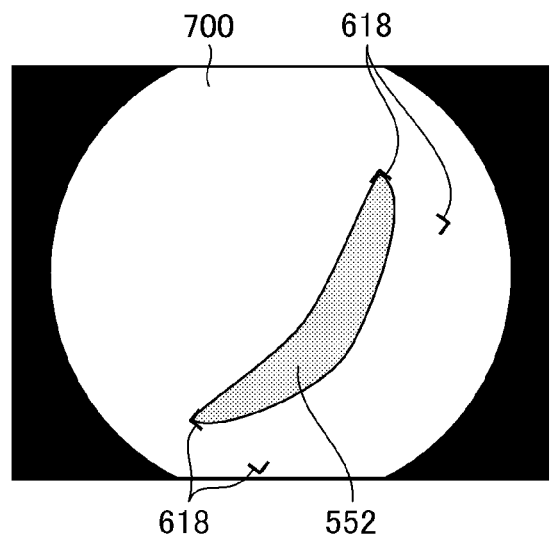

FIG. 11A is a diagram illustrating a state in which a figure 616, disposed at the sides of a rectangle (a polygon) surrounding the region of interest 552, is superimposed and displayed. FIG. 11B is a diagram illustrating a state in which figures 618 (four L-shaped figures), disposed at the vertexes of the rectangle, are superimposed and displayed. In the example illustrated in FIG. 11B, the figures 618 whose sizes and shapes are independent of the interior angles of the vertexes (all the four figures 618 are equal) are displayed.

Example 2

Figure 12A:
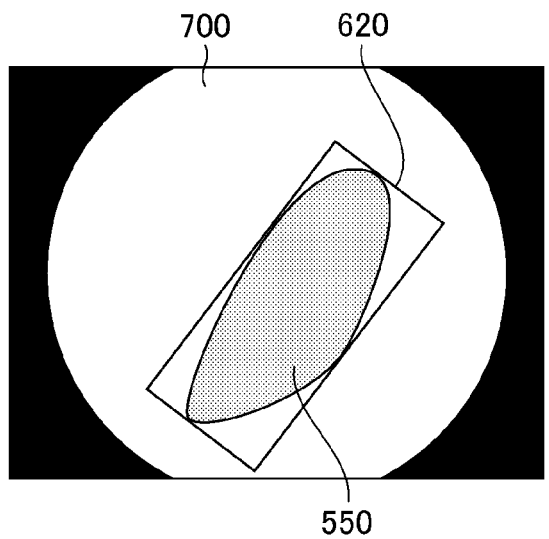
FIGS. 12A to 12C are other diagrams illustrating states in which a figure is disposed at the sides of a rectangle.
Figure 12B:
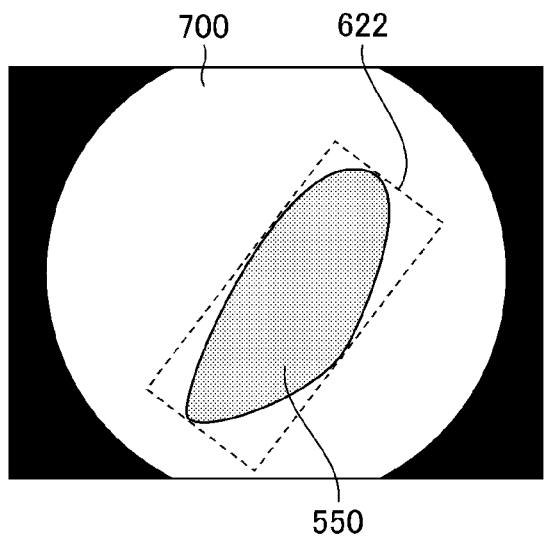
Figure 12C:
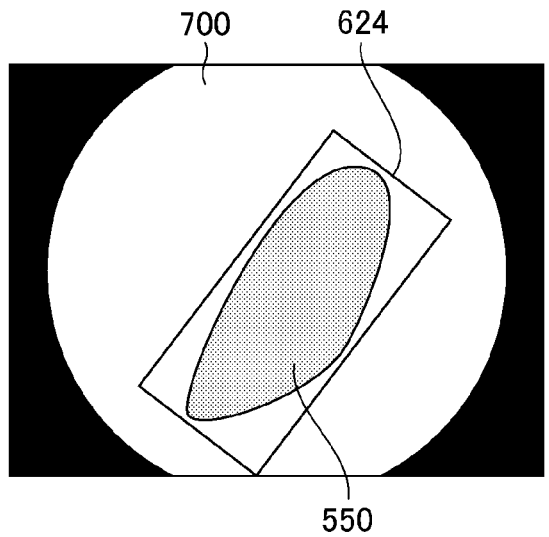

FIG. 12A is a diagram illustrating a state in which a figure 620, formed of the sides of a rectangle (a polygon) surrounding the region of interest 550, is superimposed and displayed. FIG. 12B is a diagram illustrating a state in which a figure 622 (a figure drawn with a broken line and rectangular as a whole), formed of a part of the sides of the rectangle, is superimposed and displayed. FIG. 12C is a diagram illustrating a state in which a figure 624, formed of the sides of the rectangle as in FIG. 12A, is superimposed and displayed. The figure 624 is larger than the figure 620 and has a margin between the region of interest 550 and the figure 624. Also in the other display examples, a margin can be provided as in FIG. 12C.

Example 3

Figure 13A:
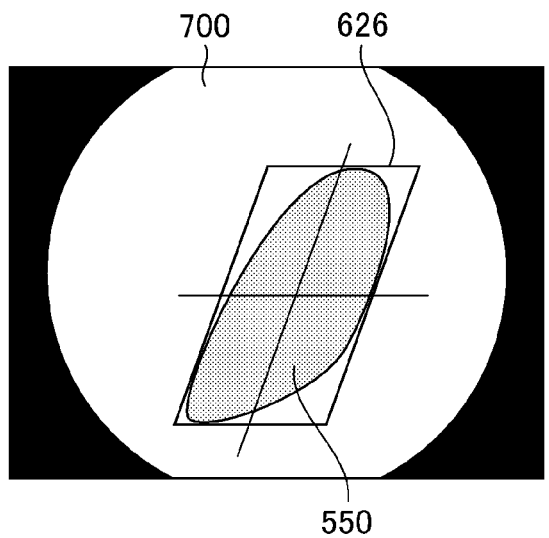
FIGS. 13A to 13C are diagrams illustrating states in which a figure is disposed at the sides of a parallelogram.
Figure 13B:
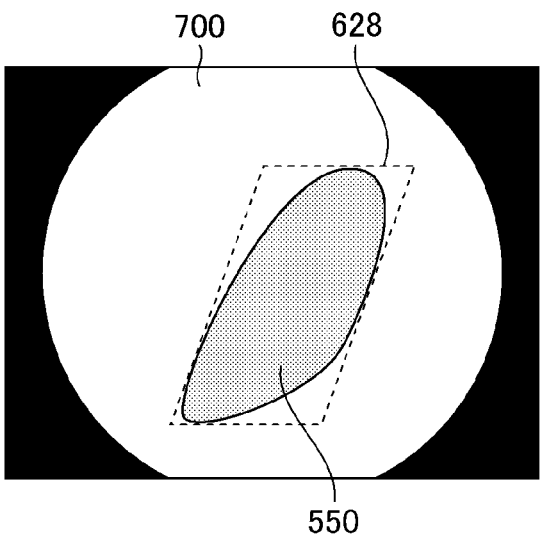
Figure 13C:
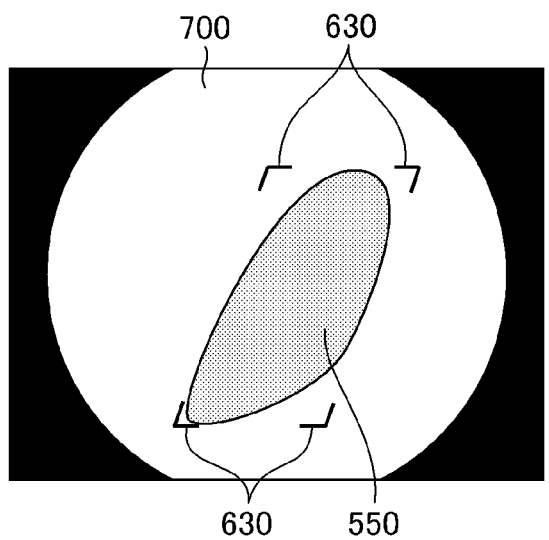

FIG. 13A is a diagram illustrating a state in which a figure 626, formed of the sides of a parallelogram (a polygon) surrounding the region of interest 550, is superimposed and displayed. FIG. 13B is a diagram illustrating a state in which a figure 628 (a figure drawn with a broken line and parallelogram-shaped as a whole), formed of a part of the sides of the parallelogram, is superimposed and displayed. FIG. 13C illustrates a state in which figures 630, disposed at the vertexes of the parallelogram and having shapes that vary according to the interior angles of the vertexes, are superimposed and displayed.

Example 4

Figure 14A:
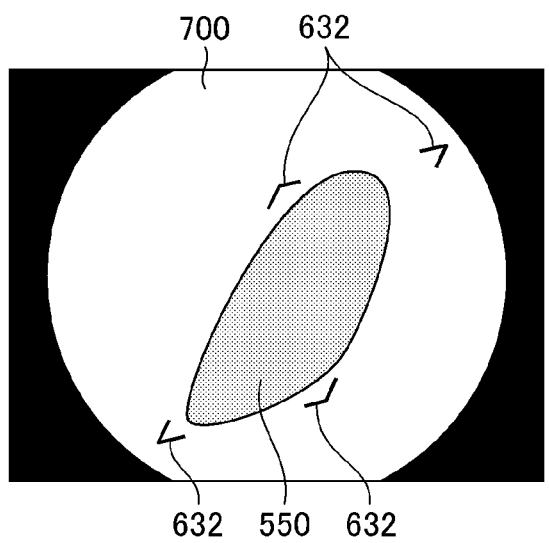
FIGS. 14A and 14B are other diagrams illustrating states in which a figure is disposed at the sides of a parallelogram.
Figure 14B:
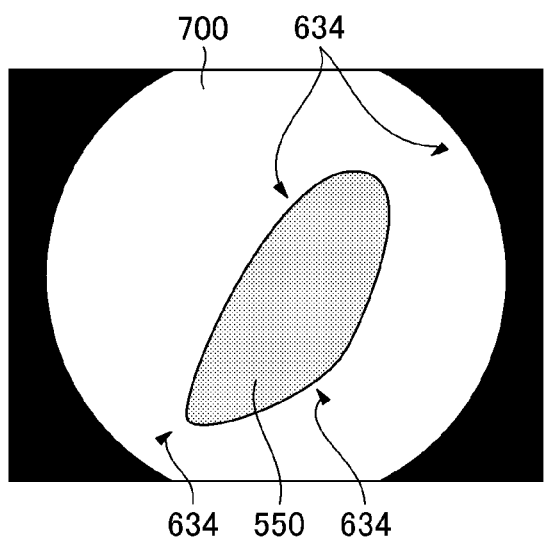

FIG. 14A is a diagram illustrating a state in which figures 632 (four L-shaped or V-shaped figures), disposed at the vertexes of a parallelogram (a polygon) surrounding the region of interest 550 and having shapes that vary according to the interior angles of the vertexes, are superimposed and displayed. FIG. 14B is a diagram illustrating a state in which figures 634 (four wedge-shaped figures oriented toward the center of the parallelogram), disposed at the vertexes of the parallelogram and having sizes and shapes that are independent of the interior angles of the vertexes, are superimposed and displayed.

Example 5

Figure 15A:
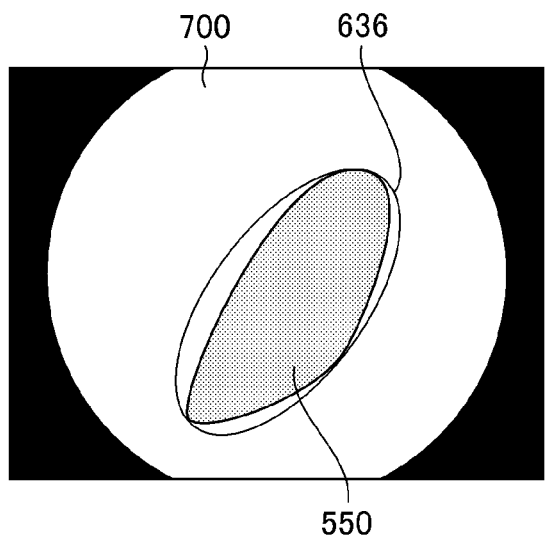
FIGS. 15A to 15C are diagrams illustrating states in which a figure is disposed on the circumference of an ellipse.
Figure 15B:
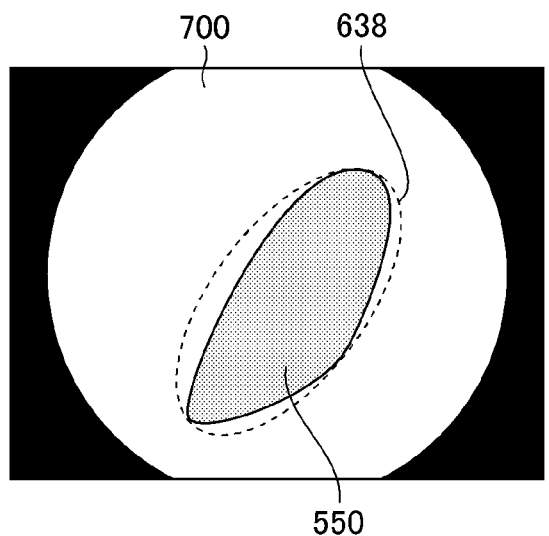
Figure 15C:
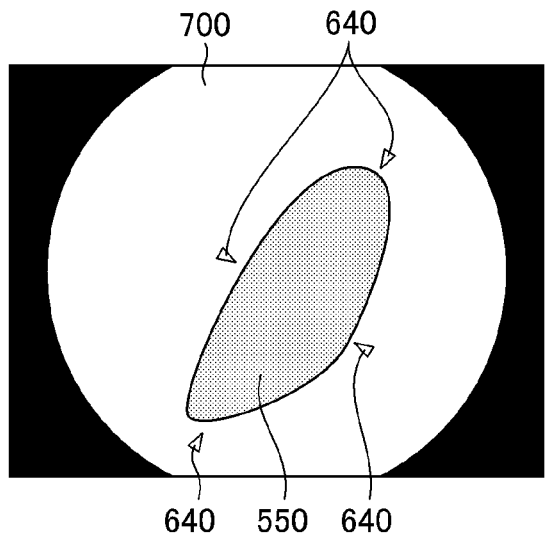

FIG. 15A is a diagram illustrating a state in which a figure 636, formed of the side of an ellipse surrounding the region of interest 550, is superimposed and displayed. FIG. 15B is a diagram illustrating a state in which a figure 638 (a figure drawn with a broken line and ellipse-shaped as a whole), formed of a part of the side of the ellipse, is superimposed and displayed. FIG. 15C illustrates a state in which figures 640 (four wedge-shaped figures oriented toward the center of the ellipse), disposed at a plurality of positions on the circumference of the ellipse and having shapes and sizes that are independent of the positions on the circumference, are superimposed and displayed.

Example 6

Figure 16A:
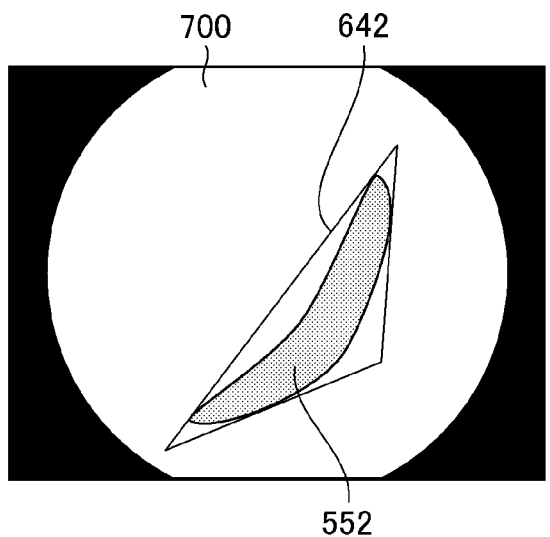
FIGS. 16A to 16D are diagrams illustrating states in which a figure is disposed at the sides of a triangle.
Figure 16B:
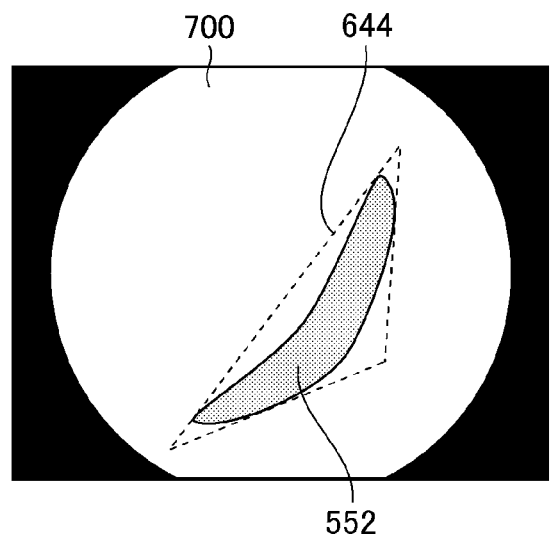
Figure 16C:
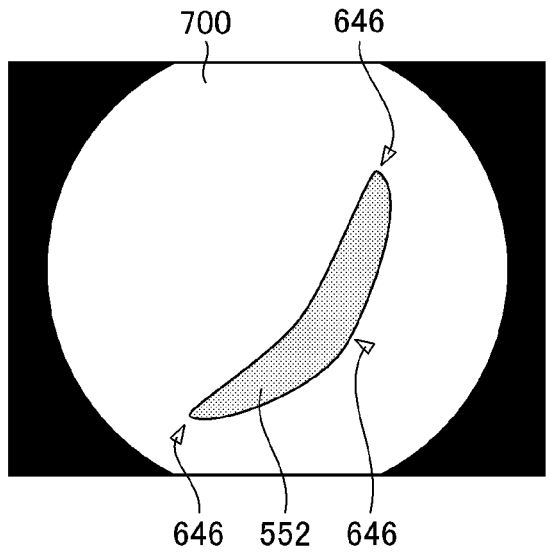
Figure 16D:
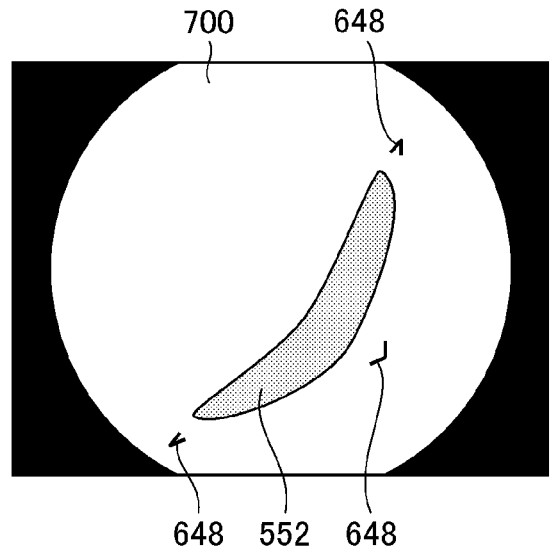

FIG. 16A is a diagram illustrating a state in which a figure 642, formed of the sides of a triangle (an aspect of a polygon) surrounding the region of interest 550, is superimposed and displayed. FIG. 16B is a diagram illustrating a state in which a figure 644 (a figure drawn with a broken line and triangular as a whole), formed of a part of the sides of the triangle, is superimposed and displayed. FIG. 16C illustrates a state in which figures 646 (three wedge-shaped figures 646), disposed at the vertexes of the triangle and having shapes and sizes that are independent of the interior angles of the vertexes, are superimposed and displayed. FIG. 16D illustrates a state in which figures 648 (three wedge-shaped figures 648), disposed at the vertexes of the triangle and having shapes that vary according to the interior angles of the vertexes, are superimposed and displayed.

Example 7

Figure 17A:
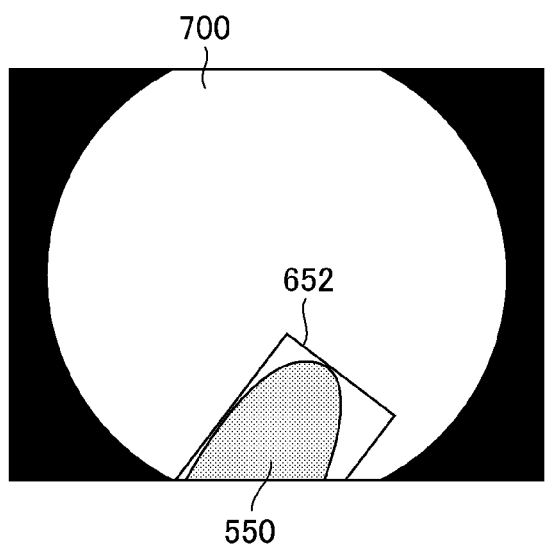
FIGS. 17A to 17C are diagrams illustrating examples of displaying a figure in a case where a part of a region of interest is depicted in an image.
Figure 17B:
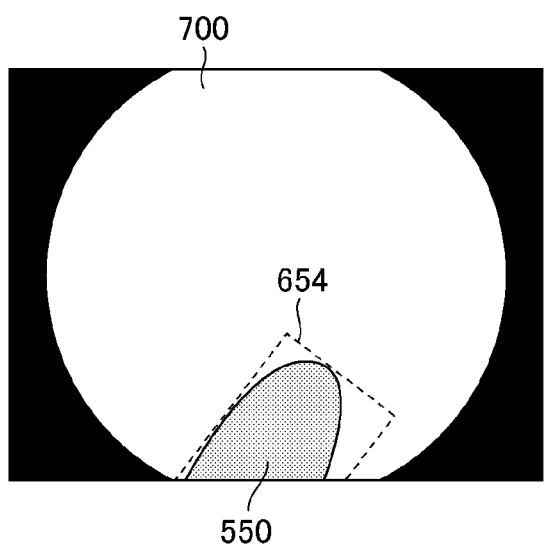
Figure 17C:
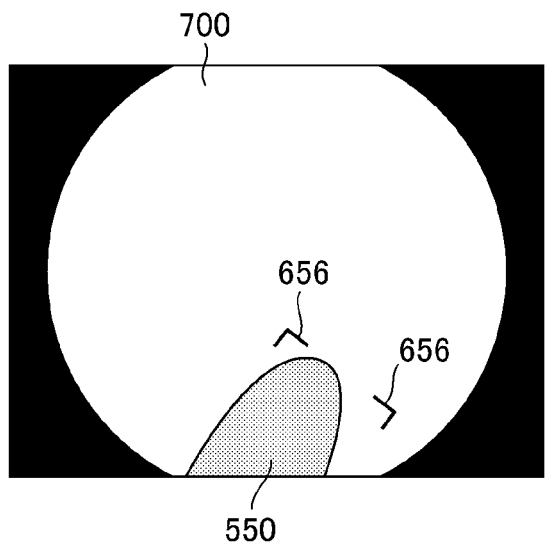

In a case where only a part of a region of interest is depicted in a time-series image, a figure may be superimposed and displayed for the depicted part. For example, in a case where a part of the region of interest 550 is depicted as illustrated in FIG. 17A, a figure formed of a prat of the sides of a rectangle, like a figure 652, can be superimposed and displayed. Similarly, a figure 654 illustrated in FIG. 17B or figure 656 illustrated in FIG. 17C may be displayed.

After the superimposition and display in step S140, the image input unit 204A determines whether or not input of the time-series image has finished (step S150: an image input step). If the determination is affirmative, the process ends. If the determination is negative, the process returns to step S110, and the next frame of the time-series image is input.

As described above, according to the endoscope system 10 (an endoscope apparatus, an image processing apparatus) and the image processing method according to the first embodiment, it is possible to assist an observer of a time-series image in performing smooth observation while attracting attention of the observer.

APPENDICES

In addition to the individual aspects of the above-described embodiment, the configurations described below are included in the scope of the present invention.

Appendix 1

A medical image processing apparatus wherein
a medical image analysis processing unit detects a region of interest on the basis of a feature quantity of pixels of a medical image, the region of interest being a region to be focused on, and
a medical image analysis result acquiring unit acquires an analysis result of the medical image analysis processing unit.

Appendix 2

A medical image processing apparatus wherein
a medical image analysis processing unit detects presence or absence of a target to be focused on on the basis of a feature quantity of pixels of a medical image, and
a medical image analysis result acquiring unit acquires an analysis result of the medical image analysis processing unit.

Appendix 3

The medical image processing apparatus wherein
the medical image analysis result acquiring unit acquires the analysis result of the medical image from a recording device in which the analysis result is recorded, and
the analysis result is either or both of the region of interest which is a region to be focused on included in the medical image and the presence or absence of the target to be focused on.

Appendix 4

The medical image processing apparatus wherein the medical image is a normal-light image acquired by radiating light in a white range or light in a plurality of wavelength ranges as the light in the white range.

Appendix 5

The medical image processing apparatus wherein
the medical image is an image acquired by radiating light in a specific wavelength range, and
the specific wavelength range is a range narrower than a white wavelength range.

Appendix 6

The medical image processing apparatus wherein the specific wavelength range is a blue or green range in a visible range.

Appendix 7

The medical image processing apparatus wherein the specific wavelength range includes a wavelength range of 390 nm or more and 450 nm or less or a wavelength range of 530 nm or more and 550 nm or less, and the light in the specific wavelength range has a peak wavelength in the wavelength range of 390 nm or more and 450 nm or less or the wavelength range of 530 nm or more and 550 nm or less.

Appendix 8

The medical image processing apparatus wherein the specific wavelength range is a red range in a visible range.

Appendix 9

The medical image processing apparatus wherein the specific wavelength range includes a wavelength range of 585 nm or more and 615 nm or less or a wavelength range of 610 nm or more and 730 nm or less, and the light in the specific wavelength range has a peak wavelength in the wavelength range of 585 nm or more and 615 nm or less or the wavelength range of 610 nm or more and 730 nm or less.

Appendix 10

The medical image processing apparatus wherein the specific wavelength range includes a wavelength range in which a light absorption coefficient is different between oxyhemoglobin and deoxyhemoglobin, and the light in the specific wavelength range has a peak wavelength in the wavelength range in which the light absorption coefficient is different between oxyhemoglobin and deoxyhemoglobin.

Appendix 11

The medical image processing apparatus wherein the specific wavelength range includes a wavelength range of 400±10 nm, a wavelength range of 440±10 nm, a wavelength range of 470±10 nm, or a wavelength range of 600 nm or more and 750 nm or less, and the light in the specific wavelength range has a peak wavelength in the wavelength range of 400±10 nm, the wavelength range of 440±10 nm, the wavelength range of 470±10 nm, or the wavelength range of 600 nm or more and 750 nm or less.

Appendix 12

The medical image processing apparatus wherein the medical image is an inside-of-living-body image depicting an inside of a living body, and the inside-of-living-body image has information about fluorescence emitted by a fluorescent substance in the living body.

Appendix 13

The medical image processing apparatus wherein the fluorescence is acquired by irradiating the inside of the living body with excitation light whose peak is 390 nm or more and 470 nm or less.

Appendix 14

The medical image processing apparatus wherein the medical image is an inside-of-living-body image depicting an inside of a living body, and the specific wavelength range is a wavelength range of infrared light.

Appendix 15

The medical image processing apparatus wherein the specific wavelength range includes a wavelength range of 790 nm or more and 820 nm or less or a wavelength range of 905 nm or more and 970 nm or less, and the light in the specific wavelength range has a peak wavelength in the wavelength range of 790 nm or more and 820 nm or less or the wavelength range of 905 nm or more and 970 nm or less.

Appendix 16

The medical image processing apparatus wherein a medical image acquiring unit includes a special-light image acquiring unit that acquires a special-light image having information about the specific wavelength range on the basis of a normal-light image that is acquired by radiating light in a white range or light in a plurality of wavelength ranges as the light in the white range, and the medical image is the special-light image.

Appendix 17

The medical image processing apparatus wherein a signal in the specific wavelength range is acquired through computation based on color information of RGB or CMY included in the normal-light image.

Appendix 18

The medical image processing apparatus including a feature quantity image generating unit that generates a feature quantity image through computation based on at least one of a normal-light image or a special-light image, the normal-light image being acquired by radiating light in a white range or light in a plurality of wavelength ranges as the light in the white range, the special-light image being acquired by radiating light in a specific wavelength range, wherein the medical image is the feature quantity image.

Appendix 19

An endoscope apparatus including:
the medical image processing apparatus according to any one of appendices 1 to 18; and
an endoscope that acquires an image by radiating at least any one of light in a white wavelength range or light in a specific wavelength range.

Appendix 20

A diagnosis assistance apparatus including the medical image processing apparatus according to any one of appendices 1 to 18.

Appendix 21

A medical work assistance apparatus including the medical image processing apparatus according to any one of appendices 1 to 18.

The embodiment of the present invention has been described above. The present invention is not limited to the above-described aspects and various modifications can be made without deviating from the spirit of the present invention.

REFERENCE SIGNS LIST

10 endoscope system
100 endoscope main body 102 handheld operation section
104 insertion section
106 universal cable
108 light guide connector
112 soft part
114 bending part
116 tip rigid part
116A distal-end-side surface
123 illumination unit
123A illumination lens
123B illumination lens
126 forceps port
130 imaging optical system
132 imaging lens
134 imaging device
136 driving circuit
138 AFE
141 air/water supply button
142 suction button
143 function button
144 imaging button
170 light guide
200 processor
202 image input controller
204 image processing unit
204A image input unit
204B information acquiring unit
204C figure calculating unit
204D display control unit
204E condition setting unit
205 communication control unit
206 video output unit
207 recording unit
208 operation unit
209 audio processing unit
209A speaker
210 CPU
211 ROM
212 RAM
300 light source apparatus
310 light source
310B blue light source
310G green light source
310R red light source
310V violet light source
330 diaphragm
340 condenser lens
350 light source control unit
400 monitor
501A region
501B region
501C button
502A region
502B region
502C button
503A region
503B region
503C button
504A region
504B region
504C button
505A region
505B region
505C button
511 button
512 button
513 button
550 region of interest
552 region of interest
600 circumscribed rectangle
602 rectangle
604 parallelogram
610 rectangle
612 parallelogram
614 ellipse
616 figure
618 figure
620 figure
622 figure
624 figure
626 figure
628 figure
630 figure
632 figure
634 figure
636 figure
638 figure
640 figure
642 figure
644 figure
646 figure
648 figure
652 figure
654 figure
656 figure
700 region
800 time-series image
901 first axis
902 second axis
903 first axis
904 second axis
905 major axis
906 minor axis
S100 to S150 individual steps of image processing method

What is claimed is:

1. An image processing apparatus comprising one or more processors configured to:
acquire a plurality of images captured in time-series;
acquire information on a region of interest in each image;
generate a circumscribed rectangle, the circumscribed rectangle being a rectangle circumscribing the region of interest and formed of two sides parallel to a horizontal axis of each image and other two sides parallel to a vertical axis of each image;
calculate a polygon or an ellipse surrounding the region of interest and having an area smaller than or equal to an area of the circumscribed rectangle; and
cause a display apparatus to display a figure such that the figure surrounds the region of interest, the figure being based on the polygon or the ellipse and being disposed at sides or vertexes of the polygon or disposed on a circumference of the ellipse or at a plurality of positions on the circumference.

2. The image processing apparatus according to claim 1, wherein the one or more processors configured to cause the display apparatus to display, as the figure, a figure disposed at the vertexes of the polygon and having a shape that varies according to interior angles of the vertexes.

3. The image processing apparatus according to claim 1, wherein one or more processors configured to cause the display apparatus to display, as the figure, a figure disposed at the vertexes of the polygon and having a size and/or a shape that is independent of interior angles of the vertexes.

4. The image processing apparatus according to claim 1, wherein one or more processors configured to cause the display apparatus to display, as the figure, a figure formed of the sides of the polygon or a part of the sides, or a figure formed of the circumference of the ellipse or a part of the circumference.

5. The image processing apparatus according to claim 1, wherein the one or more processors configured to set, to the region of interest, a first axis and a second axis intersecting the first axis, and calculate, as the polygon, a quadrangle formed of two sides parallel to the first axis and two sides parallel to the second axis.

6. The image processing apparatus according to claim 5, wherein the one or more processors configured to perform ellipse approximation on the region of interest and calculate a major axis and a minor axis of the ellipse, to calculate the polygon or the ellipse.

7. The image processing apparatus according to claim 5, wherein the one or more processors configured to calculate a rectangle as the quadrangle.

8. The image processing apparatus according to claim 1, wherein the one or more processors configured to acquire, as the plurality of images captured in time-series, an image of a subject acquired by an endoscope apparatus.

9. The image processing apparatus according to claim 1, wherein the one or more processors configured to analyze each image to acquire the information on the region of interest.

10. The image processing apparatus according to claim 1, wherein the one or more processors further configured to set, based on an instruction input by a user, the polygon or the ellipse to be calculated and/or the figure to be displayed.

11. An image processing method comprising:
    an image input step of inputting a plurality of images captured in time-series;
    an information acquisition step of acquiring information on a region of interest in each image;
    a generation step of generating a circumscribed rectangle, the circumscribed rectangle being a rectangle circumscribing the region of interest and formed of two sides parallel to a horizontal axis of each image and other two sides parallel to a vertical axis of each image;
    a figure calculation step of calculating a polygon or an ellipse surrounding the region of interest and having an area smaller than or equal to an area of the circumscribed rectangle; and
    a display control step of causing a display apparatus to display a figure such that the figure surrounds the region of interest, the figure being based on the polygon or the ellipse and being disposed at sides or vertexes of the polygon or disposed on a circumference of the ellipse or at a plurality of positions on the circumference.

* * * * *